United States Patent [19]

Yadav et al.

[11] Patent Number: 6,107,079
[45] Date of Patent: Aug. 22, 2000

[54] **DEGRADATION OF POLYCHLORINATED BIPHENYL MIXTURES IN SOIL USING *PHANEROCHAETE CHRYSOSPORIUM* IN NUTRIENT RICH, NON-LIGNINOLYTIC CONDITIONS**

[75] Inventors: Jagjit S. Yadav, Cincinnatti, Ohio; Chilekampalli A. Reddy, East Lansing, Mich.; John F. Quensen, Haslett, Mich.; James M. Tiedje, Lansing, Mich.

[73] Assignee: Board of Trustees operating Michigan State University, East Lansing, Mich.

[21] Appl. No.: 08/939,464

[22] Filed: Sep. 29, 1997

Related U.S. Application Data

[63] Continuation of application No. 08/650,323, May 20, 1996, abandoned.

[51] Int. Cl.[7] ............................... C12N 1/00; C12N 1/14
[52] U.S. Cl. ................. 435/262.5; 210/601; 435/254.1; 435/822
[58] Field of Search ................. 435/262.5, 822, 435/254.1; 210/601

[56] References Cited

U.S. PATENT DOCUMENTS

| | | | |
|---|---|---|---|
| 4,859,594 | 8/1989 | Portier | 435/172.1 |
| 4,891,320 | 1/1990 | Aust et al. | 435/262 |
| 5,476,788 | 12/1995 | Lamar et al. | 435/262.5 |
| 5,516,688 | 5/1996 | Rothmel | 435/262.5 |
| 5,583,041 | 12/1996 | Bradley et al. | 435/262.5 |

OTHER PUBLICATIONS

Abramowicz, D. A., Crit. Rev. Biotechnol. 10:241–251 (1990).
Quensen, J. F., III, et al., Appl. Environ. Microbiol. 56:2360–2369 (1990).
Bedard, D. L., et al., Appl. Environ. Microbiol. 53:1094–1102 (1987).
Boyle, A.W., et al., Biodegradation 3:285–298 (1992).
Bumpus, J.A., et al., Science 228:1434–1436 (1985).
Reddy, C.A., Current Opinion in Biotechnology 6:320–328 (1995).
Reddy, C.A., J. Biotechnol. 30:91–107 (1993).
Kohler, A., et al., Appl. Microbiol. Biotechnol. 29:618–620 (1988).
Hammel, K.E., Oxidation of Aromatic Pollutants by Lignin—degrading Fungi and Their Extra–cellular Peroxidases, p. 41–60. In H. Sigel and A. Sigel (ed.), Metal ions in Biological Systems, vol. 28. Degradation of Environmental Pollutants by Microorganisms and Their Metalloenzymes. Marcel Dekker, Inc, N.Y. (1992).
Yadav, J.S., et al., Biotechnol. Lett. 14:1089–1092 (1992).
Yadav, J.s., et al., Appl. Environ. Microbiol. 59:2904–2908 (1993).
Yadav, J.S., et al., Appl. Environ. Microbiol. 61:677:680 (1995).
Yadav, J.S., et al., Appl. Environ. Microbiol. 59:756–762 (1993).
Thomas, D.R., et al., Biotechnol. Bioeng. 40:1395–1402 (1992).
Eaton, D.C., Enzyme Microb. Technol. 7:194–196 (1985).
Schulz, D.E., et al., Environ. Sci. Technol. 23:852–858 (1989).
Kohler, H.P.E., et al., Appl. Environ. Microbiol. 54:1940–1945 (1988).
Dmochewitz, S., et al., Chemosphere 17:11–121 (1988).
GE Progress Report, General Electric Company Research and Develop. program, etc. Aug. 1, 1992–Jul. 31, 1993 pp. 117–127 & 129–141 (1993).
Lamar, R.T. and D.M. Dietrich, Appl. Environ. Microbiol. 56:3093–3100 (1990).

*Primary Examiner*—David M. Naff
*Assistant Examiner*—Deborah K. Ware
*Attorney, Agent, or Firm*—Ian C. McLeod

[57] ABSTRACT

Substantial degradation of polychlorinated biphenyl (PCB) mixtures is carried out using the white rot fungus *Phanerochaete chrysosporium*, under nutrient, carbon and nitrogen source rich, non-ligninolytic conditions. The PCBs with various numbers of ortho, meta, and para chlorines were extensively degraded, indicating relative nonspecificity for the position of chlorine substitutions on the biphenyl ring. Maximal degradation of PCBs in a mixture was observed in malt extract medium (18.4% on a molar basis), in which most of the individual PCBs were degraded.

11 Claims, 4 Drawing Sheets

DEGRADATION OF POLYCHLORINATED BIPHENYL MIXTURES IN SOIL USING *PHANEROCHAETE CHRYSOSPORIUM* IN NUTRIENT RICH, NON-LIGNINOLYTIC CONDITIONS

This application is a continuation of application Ser. No. 08/650,323 filed on May 20, 1996, now abandoned.

GOVERNMENT RIGHTS

This invention was developed under National Science Foundation Grant B1R 91-2006 and U.S. Department of Energy Grant DE-FG02-85ER 13369. The U.S. Government has certain rights to this invention.

BACKGROUND OF THE INVENTION

(1) Field of the Invention

The present invention relates to the degradation of mixtures of polychlorinated biphenyls (PCBs) which occur as contaminants in the environment using a white rot fungus, *Phanerochaete chrysosporium*. In particular, the present invention relates to the degradation of mixtures of PCBs which contain up to about 60% by weight of chlorine and an average of 3 to 6 chlorine atoms per biphenyl molecule in contaminated compositions, particularly soil.

(2) Description of Related Art

Polychlorinated biphenyls (PCBs) are a family of compounds with a wide range of industrial applications in heat transfer fluids, dielectric fluids, hydraulic fluids, flame retardants, plasticizers, solvent extenders, and organic diluents. In the United States and the United Kingdom, complex PCB mixtures were manufactured under the trade name AROCLOR; among these are AROCLORS 1242, 1254, and 1260, which contain 42, 54 and 60% chlorine by weight (the last two digits represent the percent chlorine by weight), with an average of 3, 5 and 6 chlorines per biphenyl molecule, respectively. Aroclors consist of many congeners which differ in the number and distribution of chlorines on the biphenyl nucleus. About 150 congeners have been reported in the environment. PCBs have entered into soil and sediment environments as a result of improper disposal of industrial PCB wastes and leakage of PCBs from electric transformers. Their chemical inertness, due to a stable molecular structure and hydrophobicity, is believed to be responsible for their low biodegradation in ecosystems, leading to their persistence in the environment.

Some PCB congeners have been shown to be transformed by both aerobic and anaerobic bacteria (Abramowicz, D. A., Crit. Rev. Biotechnol. 10:241–251 (1990); and Quensen, J. F., III, et al., Appl. Environ. Microbiol. 56:2360–2369 (1990)). The aerobic biodegradation of PCBs is generally limited to less-chlorinated congeners (5 or fewer chlorines per biphenyl molecule) by a mechanism involving deoxygenase attack of the aromatic ring (Bedard, D. L., et al., Appl. Environ. Microbiol. 53:1094–1102 (1987); and Boyle, A. W, et al., Biodegradation 3:285–298 (1992)). The more-chlorinated congeners are generally recalcitrant to aerobic degradation. For instance, the aerobic microbial degradation of most of the congeners of Aroclor 1242 and that of some of the congeners of Aroclor 1254 have been demonstrated in the past, but there has been no convincing evidence to date for aerobic microbial degradation of Aroclor 1260. In contrast to aerobic biodegradation, PCBs undergo reductive dechlorination under anaerobic conditions, leading to the transformation of the more-chlorinated congeners to less-chlorinated congeners usually leaving the biphenyl ring intact. Chlorines substituted in the ortho position are generally recalcitrant to anaerobic dechlorination (GE Progress Report, General Electric Company Research and Development program for the destruction of PCBs: twelfth progress report for the period Aug. 1, 1992–July 31, pages 117–127 & 129–141 1993. General Electric Co. Corporate Research and Development, Schenectady, N.Y. (1993); and Quensen, J. F., et al, Appl. Environ. Microbiol. 56:2360–2369 (1990)).

*Phanerochaete chrysosporium*, a lignin-degrading white rot fungus, is known to mineralize a wide range of chloroaromatic environmental pollutants to $CO_2$ (Bumpus, J. A., et al., Bioassays 6:116–120 (1987); Reddy, C. A., Current Opinion in Biotechnology 6:320–328 (1995); and Hammel, K. E., Oxidation Of Aromatic Pollutants By Lignin-degrading Fungi and Their Extracellular Peroxidases, p. 41–60. In H. Sigel and A. Sigel (ed.), Metal ions in biological systems, vol. 28. Degradation Of Environmental Pollutants By Microorganisms And Their Metalloenzymes. Marcel Dekker, Inc., New York (1992)). Degradation of many of these pollutants was reported to be mediated by the lignin-degrading enzyme system of this organism. Major components of the lignin-degrading enzyme system include lignin peroxidases (LIPs), Mn (II)-dependent peroxidases (MNPs), and the $H_2O_2$-producing enzyme system, which are induced during secondary metabolism, under nutrient-limiting culture conditions, but not under nutrient-rich conditions (Reddy, C. A., J. Biotechnol. 30:91–107 (1993)). More recently, a number of chloroaromatic pollutants were shown to be degraded by *P. chrysosporium* under nonligninolytic culture conditions (such as in defined high-N medium or nutrient-rich malt extract medium) when LIPs and MNPs are not produced (Kohler, A., et al., Appl. Microbiol. Biotechnol. 29:618–620 (1988); Yadav, J. S., et al., Biotechnol. Lett. 14:1089–1092 (1992); Yadav, J. S., et al., Appl. Environ. Microbiol. 59:2904–2908 (1993); and Yadav, J. S., et al., Appl. Environ. Microbiol. 61:677–680 (1995)).

Previous studies (Bumpus, J. A., et al., Science 228:1434–1436 (1985); and Thomas, D. R., et al., Biotechnol. Bioeng. 40:1395–1402 (1992)) demonstrated low levels of mineralization of 0.9 to 1.1% for individual PCB congeners, such as 3,3',4,4'-chlorobiphenyl (CB), 2,2',4,4'-CB, and 2,2',4,4',5,5'-CB when these were added to cultures at a low concentration (0.036 to 1.55 ppm) under ligninolytic culture conditions, i.e., at 2.4 mM ammonia and 56 mM glucose. Eaton (Eaton, D. C., Enzyme Microb. Technol. 7:194–196 (1985)) reported $\leq 9\%$ mineralization when 0.25 ppm of Aroclor 1254 was added to such cultures. Although these data suggested mineralization of selected PCBs and PCB mixtures of *P. chrysosporium*, some skepticism of the reported PCB-degrading potential of this organism was expressed because of the low concentrations tested (Abramowicz, D. A., Crit. Rev. Biotechnol. 10:241–251 (1990)). There are no convincing data on the ability of the fungus to show substantial degradation of PCB mixtures at environmentally relevant concentrations or at levels degraded by known bacterial systems. Such data are needed to evaluate the PCB bioremediation potential of *P. chrysosporium*. Furthermore, relative degradation of individual PCB congeners in different Aroclor mixtures is not known. Such information is useful for comparing the nature and extent of degradation of various PCB congeners in fungal versus bacterial systems (Abramowicz, D. A., Crit. Rev. Biotechnol. 10:241–251 (1990)). Also, degradation of the highly chlorinated PCB mixture Aroclor 1260 has not been demonstrated before in either bacterial or fungal systems (Abramowicz, D. A., Crit. Rev. Biotechnol. 10:241–251 (1990)). Also, PCB mixture degradation by *P. chrysospo-*

*rium* under non-ligninolytic conditions—(i.e. under nitrogen-rich and carbon-rich conditions when LIPs and MNPs are not produced) has not been demonstrated. This is important because nutrient-rich conditions prevail at some contamination sites.

OBJECTS

It is therefore an object of the present invention to provide a method for the degradation of complex mixtures of PCBs such as occur in AROCLOR 1242, 1254 and 1260 under both nutrient-limiting and non-limiting conditions. It is particularly an object of the present invention to provide a method which is simple, rapid, and easily adaptable to PCB-contaminated environments and economical. These and other objects will become increasingly apparent by reference to the following description and the drawings.

DESCRIPTION OF PREFERRED EMBODIMENTS

Figure 1:
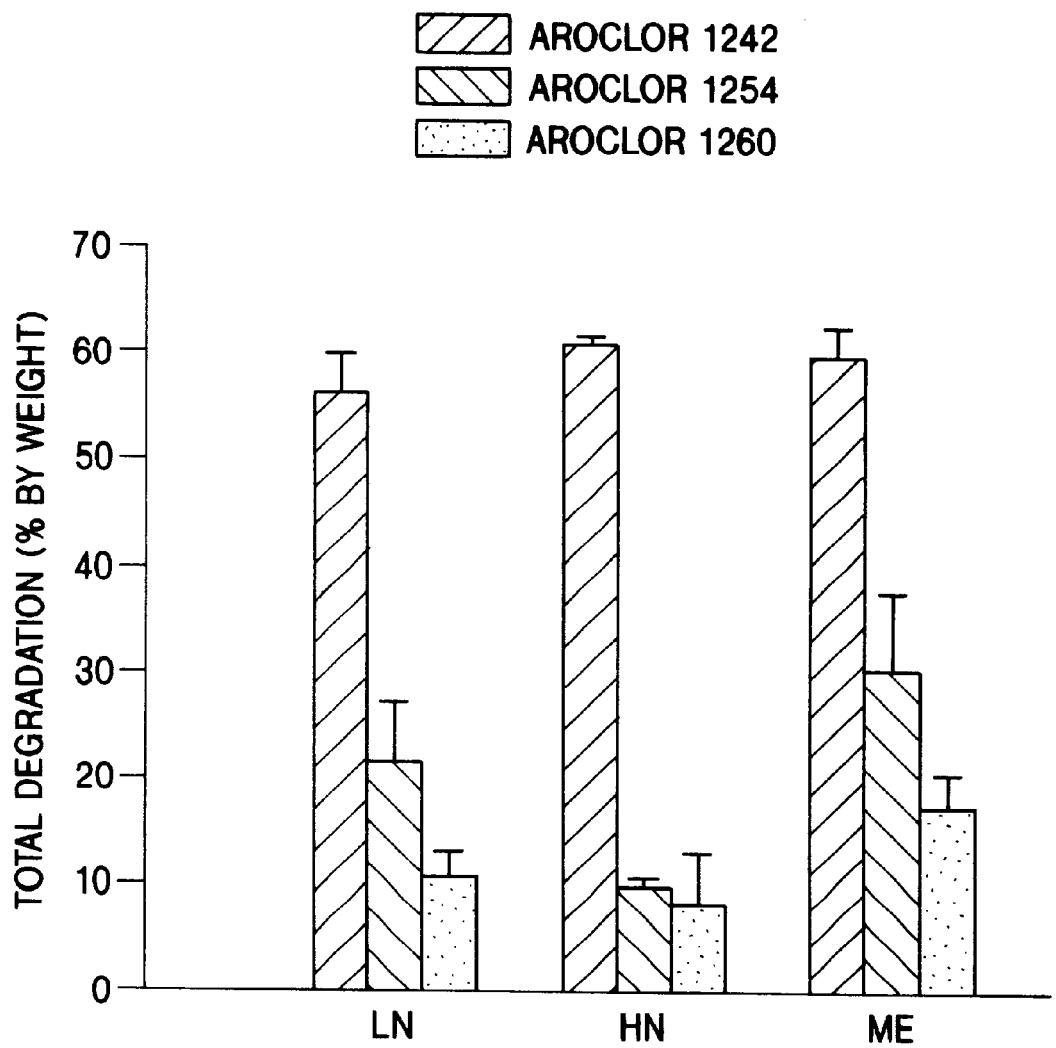
FIG. 1 is a graph showing loss of total PCB content in AROCLORS 1242, 1254 and 1260 by *P. chrysosporium* when grown in different media. Cultures were incubated for 30 days. Values presented are means of triplicate samples. Low nitrogen (LN), 2,4 mM N; High nitrogen (HN), 24 mM N (ten times difference).

The present invention relates to a method for degrading a complex mixture of polychlorinated biphenyls containing an average between 3 and 6 chlorine atoms per biphenyl and up to about 60% by weight of chlorine in a contaminated composition which comprises: mixing the composition with *Phanerochaete chrysosporium* under nitrogen and carbon rich, non-ligninolytic conditions; and degrading of the mixture of polychlorinated biphenyls in the composition with the *Phanerochaete chrysosporium*.

Under environmental conditions where PCBs contaminate soils or aquifers, there is usually some carbon and nitrogen which serve as sources of nutrients for the white rot fungus. For bioremediation applications, the soil is amended to include a carbon source and a nitrogen source to stimulate fungal growth. Carbon sources are usually carbohydrates. In the laboratory, simple sugars, such as glucose, are used to grow the fungus to provide fungal compositions which can be used in the field. A preferred carbon and nitrogen source was malt extract for growing the fungus for laboratory use. A peptic digest of the milk protein casein was also used as a source of nitrogen for growing the cultures in the laboratory. Inexpensive sources of carbon for use of the fungal compositions in the field with the PCBs are cellulose, hemicellulose and starch. Animal and vegetable materials are inexpensive sources of nitrogen for field use. The nitrogen source can also be ammonium ion (from ammonium nitrate) or urea or commercial plant fertilizers also serve as sources of nitrogen and minerals. Sources of nitrogen and carbon are well known to those skilled in the art.

A medium for growing the fungal cultures in the laboratory included up to 5% by weight yeast extract and more than 56 mM glucose as a carbon source and 24 mM of ammonium ion as the nitrogen source. Equivalent amounts of the other carbon and nitrogen sources can be used to grow the fungus in the laboratory or in the field.

Malt extract is a carbon source. There is between 0.1 and 5 percent of the malt extract in the contaminated composition. The carbon source can be added to the contaminated composition during the degradation of the PCBs.

EXAMPLE 1

In this Example 1, degradation of relatively high concentrations of Aroclors 1242, 1254 and 1260 by *P. chrysosporium* under varied culture conditions using congener-specific gas chromatographic (GC) analysis is described. The degradation results are shown in Table 1.

TABLE 1

Comparative degradation of Aroclors 1242 and 1254 by *P. chrysosporium* in different media[a]

| Peak no. | Congener structure[b] | No. of chlorines/biphenyl | | Mol wt (avg) | Degradation (%) of congeners in different culture media[c] | | | | | |
|---|---|---|---|---|---|---|---|---|---|---|
| | | Total (avg) | Ortho (avg) | | Aroclor 1242 | | | Aroclor 1254 | | |
| | | | | | LN | HN | ME | LN | HN | ME |
| 1 | 2- | 1 | 1 | 188.7 | 100 (0) | 100 (0) | 100 (0) | | | |
| 2 | 3- | 1 | 0 | 188.7 | | | | | | |
| 3 | 4- | 1 | 0 | 188.7 | 100 (0) | 100 (0) | 100 (0) | | | |
| 4 | 2-2, 26 | 2 | 2 | 223.1 | 93 (1) | 96 (0) | 97 (0) | | | |
| 5 | 24, 25 | 2 | 1 | 223.1 | 88 (1) | 93 (2) | 93 (1) | | | |
| 6 | 2-3 | 2 | 1 | 223.1 | 89 (1) | 95 (1) | 98 (9) | | | |
| 7 | 2-4, 23 | 2 | 1 | 223.1 | 85 (1) | 92 (1) | 95 (0) | | | |
| 8 | 26-2 | 3 | 3 | 257.5 | 93 (1) | 93 (2) | 95 (0) | | | |
| 9 | 34, 3-4 | 2 | 0 | 223.1 | 82 (1) | 78 (1) | 83 (3) | | | |

TABLE 1-continued

Comparative degradation of Aroclors 1242 and 1254 by *P. chrysosporium* in different media[a]

| Peak no. | Congener structure[b] | No. of chlorines/ biphenyl Total (avg) | Ortho (avg) | Mol wt (avg) | Degradation (%) of congeners in different culture media[c] | | | | | |
|---|---|---|---|---|---|---|---|---|---|---|
| | | | | | Aroclor 1242 | | | Aroclor 1254 | | |
| | | | | | LN | HN | ME | LN | HN | ME |
| 10 | 25-2, 4-4 | 2.75 | 1.51 | 249 | 78 (0) | 85 (3) | 81 (2) | | | |
| 11 | 24-2 | 3 | 2 | 257.5 | 79 (1) | 85 (3) | 83 (2) | | | |
| 12 | 26-3, 236 | 3 | 2 | 257.5 | 81 (0) | 86 (1) | 91 (1) | | | |
| 13 | 23-2, 26-4 | 3 | 2 | 257.5 | 82 (0) | 89 (2) | 94 (1) | | | |
| 14 | 35-2 (26-26) | 3 | 1 | 257.5 | 68 (3) | 85 (21) | 62 (5) | | | |
| 15 | 245- | 3 | 1 | 257.5 | 64 (4) | 72 (2) | 52 (5) | | | |
| 16 | 25-3 | 3 | 1 | 257.5 | 58 (5) | 66 (2) | 49 (5) | | | |
| 17 | 24-3 | 3 | 1 | 257.5 | 65 (4) | 73 (3) | 78 (4) | | | |
| 18 | 25-4 | 3 | 1 | 257.5 | 54 (5) | 62 (2) | 40 (5) | | | |
| 19 | 24-4 (246-2) | 3 | 1 | 257.5 | 69 (3) | 71 (2) | 76 (4) | | | |
| 20 | 34-2, 234, 23-3, 25-26 | 3.06 | 1.12 | 259.5 | 65 (4) | 71 (2) | 77 (3) | | | |
| 21 | 23-4 (24-26) | 3 | 1 | 257.5 | 57 (6) | 65 (2) | 71 (4) | | | |
| 22 | 236-2 | 4 | 3 | 292 | 66 (2) | 67 (2) | 54 (4) | | | |
| 23 | 23-26 | 4 | 3 | 292 | 70 (4) | 61 (2) | 81 (2) | | | |
| 24 | 25-25, 26-35 | 4 | 2 | 292 | 40 (5) | 44 (1) | 26 (4) | 45 (3) | 28 (1) | 33 (5) |
| 25 | 24-25 | 4 | 2 | 292 | 43 (5) | 48 (1) | 31 (4) | 58 (2) | 32 (2) | 53 (4) |
| 26 | 24-24 | 4 | 2 | 292 | 47 (6) | 52 (0) | 54 (6) | | | |
| 27 | 245-2, 246-4 | 4 | 2 | 292 | 49 (6) | 54 (0) | 49 (5) | | | |
| 28 | 34-3 | 3 | 0 | 257.5 | | | | | | |
| 29 | 23-25 | 4 | 2 | 292 | 48 (5) | 56 (1) | 58 (5) | 81 (0) | 75 (2) | 94 (0) |
| 30 | 23-24, 236-3, 34-4 | 3.42 | 0.84 | 272.4 | 43 (6) | 48 (3) | 52 (4) | 72 (1) | 67 (3) | 88 (1) |
| 31 | 26-34, 234-2, 236-4, 25-35 | 4 | 1.75 | 292 | 46 (6) | 48 (1) | 47 (3) | 57 (2) | 39 (2) | 70 (7) |
| 32 | 236-26 | 5 | 4 | 326.4 | | | | | | |
| 33 | 23-23 | 4 | 2 | 292 | 38 (7) | 32 (4) | 26 (3) | | | |
| 34 | 235-3, 245-3, 246-24, 246-25 | 4.2 | 1.4 | 298.9 | 13 (10) | 0 (0) | 0 (0) | | | |
| 35 | 23-35, 235-4 | 4 | 1 | 292 | | | | | | |
| 36 | 245-4 (235-26) | 4 | 1 | 292 | 23 (7) | 23 (8) | 16 (4) | 30 (4) | 14 (0) | 35 (11) |
| 37 | 25-34, 345-2 | 4 | 1 | 292 | 25 (7) | 29 (9) | 18 (3) | 26 (4) | 8 (0) | 31 (7) |
| 38 | 236-25, 245-26, 24-34 | 4.04 | 1.08 | 293.5 | 34 (7) | 35 (5) | 46 (6) | 0 (0) | 20 (1) | 33 (5) |
| 39 | 234-3, 236-24 | 4.95 | 2.9 | 324.7 | 31 (6) | 31 (6) | 24 (3) | 67 (1) | 36 (4) | 45 (11) |
| 40 | 246-246-CB (surrogate) | 6 | 4 | 360.9 | | | | | | |
| 41 | 23-34, 234-4 | 4 | 1 | 292 | 26 (7) | 27 (6) | 28 (4) | 22 (4) | 6 (1) | 24 (7) |
| 42 | 245-25, 235-24 | 5 | 2 | 326.4 | 14 (7) | 18 (8) | 0 (0) | 28 (4) | 13 (2) | 31 (7) |
| 43 | 245-24 | 5 | 2 | 326.4 | | | | | | |
| 44 | 236-246, 2356-3, 246-34 | 5.33 | 2.67 | 337.8 | | | | | | |
| 45 | 245-23, 2345-2 (2356-26) | 5 | 2 | 326.4 | 18 (7) | 18 (7) | 17 (3) | 35 (3) | 19 (1) | 51 (5) |
| 46 | 234-25, 2346-4, 235-35 | 5 | 1.67 | 326.4 | 6 (10) | 11 (6) | 0 (0) | 44 (2) | 20 (1) | 62 (3) |
| 47 | 234-24 | 5 | 2 | 326.4 | | | | 74 (0) | 58 (4) | 87 (1) |
| 48 | 236-236 | 6 | 4 | 360.9 | | | | 16 (6) | 0 (0) | 4 (4) |
| 49 | 34-34, 236-34 | 4.69 | 1.38 | 315.8 | 10 (6) | 11 (10) | 13 (2) | 24 (5) | 8 (2) | 41 (7) |
| 50 | 2356-25 | 6 | 3 | 360.9 | 12 (7) | 14 (11) | 11 (1) | 13 (5) | 0 (0) | 9 (5) |
| 51 | 235-236, 345-25, 2346-25 | 5.87 | 2.74 | 356.3 | | | | 21 (7) | 27 (1) | 63 (5) |
| 52 | 245-34, 236-245, 2345-3 | 5.32 | 1.64 | 337.5 | | | | 18 (4) | 0 (0) | 0 (0) |
| 53 | 2356-23, 2345-26, 2345-4 | 5.62 | 2.24 | 347.8 | | | | 8 (8) | 0 (0) | 10 (5) |
| 54 | 235-245, 2346-35 | 6 | 2 | 360.9 | | | | 6 (7) | 0 (0) | 0 (0) |
| 55 | 245-245 | 6 | 2 | 360.9 | 0 (0) | 22 (10) | 37 (26) | 1 (5) | 0 (0) | 0 (0) |
| 56 | 234-236, 234-34 | 5.62 | 2.24 | 347.8 | 6 (9) | 4 (10) | 6 (1) | 19 (4) | 0 (0) | 16 (7) |
| 57 | 2345-25 | 6 | 2 | 360.9 | | | | 8 (6) | 0 (0) | 14 (9) |
| 58 | 2356-236 | 7 | 4 | 395.3 | | | | | | |
| 59 | 2345-24 | 6 | 2 | 360.9 | | | | 14 (7) | 0 (0) | 28 (16) |
| 60 | 2346-236 | 7 | 4 | 395.3 | | | | | | |
| 61 | 234-245, 2356-34 | 6 | 2 | 360.9 | | | | 10 (4) | 0 (0) | 17 (8) |
| 62 | 2346-34 | 6 | 2 | 360.9 | | | | 4 (6) | 0 (0) | 6 (10) |
| 63 | 2356-235 | 7 | 3 | 395.3 | | | | 0 (0) | 0 (0) | 0 (0) |
| 64 | 2346-235 | 7 | 3 | 395.3 | | | | | | |
| 65 | 2356-245, 2345-246 | 7 | 3 | 395.3 | | | | | | |
| 66 | 2346-245 | 7 | 3 | 395.3 | | | | | | |
| 67 | 245-345 | 6 | 1 | 360.9 | | | | 2 (6) | 0 (0) | 2 (8) |
| 68 | 23456-25 | 7 | 3 | 395.3 | | | | | | |
| 69 | 2345-236, 23456-24 | 7 | 3 | 395.3 | | | | 6 (10) | 0 (0) | 0 (0) |
| 70 | 2356-234 | 7 | 3 | 395.3 | | | | | | |
| 71 | 2346-234, 2345-34, 2356-2356 | 6.71 | 2.41 | 386.4 | | | | 4 (6) | 0 (0) | 3 (10) |
| 72 | 23456-23, 2346-2356, 23456-246 | 7.87 | 3.87 | 425.4 | | | | | | |
| 73 | 2345-235, 23456-35 | 7 | 2 | 395.3 | | | | | | |
| 74 | 2345-245 | 7 | 2 | 395.3 | | | | 0 (0) | 0 (0) | 6 (11) |
| 75 | 2356-345 | 7 | 2 | 395.3 | | | | | | |

TABLE 1-continued

Comparative degradation of Aroclors 1242 and 1254 by *P. chrysosporium* in different media[a]

| Peak no. | Congener structure[b] | No. of chlorines/ biphenyl Total (avg) | Ortho (avg) | Mol wt (avg) | Degradation (%) of congeners in different culture media[c] Aroclor 1242 LN | HN | ME | Aroclor 1254 LN | HN | ME |
|---|---|---|---|---|---|---|---|---|---|---|
| 76 | 2346-345 | 7 | 2 | 395.3 | | | | | | |
| 77 | 23456-236 | 8 | 4 | 429.8 | | | | | | |
| 78 | 2345-234 | 7 | 2 | 395.3 | | | | 0 (0) | 0 (0) | 4 (11) |
| 79 | 23456-34 | 7 | 2 | 395.3 | | | | | | |
| 80 | 2356-2345 | 8 | 3 | 429.8 | | | | | | |
| 81 | 2345-2346, 23456-245 | 8 | 3 | 429.8 | | | | | | |
| 82 | 2345-345 | 7 | 1 | 395.3 | | | | | | |
| 83 | 23456-234 | 8 | 3 | 429.8 | | | | | | |
| 84 | 23456-2356 | 9 | 4 | 464.2 | | | | | | |
| 85 | 2345-2345 | 8 | 2 | 429.8 | | | | | | |
| 86 | 23456-345 | 8 | 2 | 429.8 | | | | | | |
| 87 | 23456-2345 | 9 | 3 | 464.2 | | | | | | |
| 88 | OCN (internal standard) | | | | | | | | | |

[a]Initial concentration of Aroclor added, 10 ppm; incubation period, 30 days.
[b]The numbering scheme used for the congener structure was adapted from the system of Quensen et al. (12). For example, the structure of peak number 43 is shown as 245-24-CB for ease of presentation and readability rather than the more conventional designation, 2,2', 4,4',5-CB. Note that some of the peaks represent more than one cogener, as these are not resolved by the GC technique used. OCN, octachloronaphthalene.
[c]Percent degradation represents the net decrease (percent by weight) in experimental cultures, compared with that of the heat-killed controls. Minor peaks representing <0.1-$\mu$mol/liter concentration were ignored for calculation of percent degradation, to avoid confusion due to variability. Values presented are means of triplicate samples and are standardized on the recovery of the surrogate PCB congener 246-246-CB. Values in parentheses represent standard deviations as percentages of the means. Blank space across from a peak number represents absence of that peak in the given Aroclor.

The results show (i) extensive degradation of most of the PCB congeners in AROCLOR 1242 and many of the congeners in AROCLOR 1254, including the ortho-substituted congeners under both nutrient-limited and nutrient-rich culture conditions and, (ii) particularly show degradation of AROCLOR 1260 by *P. chrysosporium*.

MATERIALS AND METHODS

Strain. *P. chrysosporium* ME-446 (ATCC 34541) was used in the present study and was maintained on malt extract agar slants as previously described (Yadav, J. S., et al., Appl. Environ. Microbiol. 59:756–762 (1993)).

Chemicals. AROCLORS 1242, 1254 and 1260 were obtained from Ultra Scientific (North Kingstown, R.I.). A stock solution (10%, wt/vol) of each of the AROCLORS was prepared in acetone and stored in a freezer (−20° C.) until use.

Media and Inoculum. Low-nitrogen basal III medium (LN medium, 2.4 mM $NH_4^+$) and high-N medium (HN medium; 2+ mM $NH_4^+$) were described previously (Yadav, J S., et al., Appl. Environ. Microbiol. 59:756–762 (1993)). Malt extract medium (ME medium) contained 2% malt extract (Difco Laboratories, Detroit, Mich.), 2% glucose, and 0.1% Bacto Peptone, pH 4.5. A blended mycelial inoculum was prepared in LN medium (without Tween 80) as described previously (Yadav, J. S., et al., Appl. Environ. Microbiol. 59:756–762 (1993)) and was used at the 10% (vol/vol) level.

Culture conditions. The organism was grown in static liquid cultures (10 ml) in 160-ml glass serum bottles sealed with Teflon-coated rubber stoppers. The three different media used were LN medium (2.4 mM N and 56 mM glucose), HN medium (24 mM N and 56 mM glucose), and ME medium (8 mM N and 112 mM glucose plus additional C as malt extract). LN medium allows the expression of the lignin-degrading enzyme system, including LIPs and MNPs, while HN and ME media do not allow expression of LIPs and MNPs (Reddy C. A., J. Biotechnol. 30:91–107 (1993); and Yadav, J. S., et al., Appl. Environ. Microbiol. 59:756–762 (1993)). The media were spiked with Aroclor 1242, 1254 or 1260 to a final concentration of 10 ppm, followed by incubation at 37° C. for 15 or 30 days. Heat-killed controls were prepared, using parallel autoclaved cultures which were pregrown for 7 days under identical conditions. Mycelial mass in these control cultures was equivalent to that in experimental cultures. The cultures were oxygenated (Yadav, J. S., et al., Appl. Environ. Microbiol. 59:756–762 (1993)) at 3-day intervals for 15 days and at 6-day intervals thereafter. Parallel heat-killed controls were similarly oxygenated to correct for any vapor loss of PCBs in experimental cultures. However, our results showed that vapor loss is not a problem, as the actual PCB recoveries in our study were very similar to those obtained in earlier anaerobic studies (i.e., closed system) on PCB biodegradation (Quensen, J. F., III, Appl. Environ. Microbiol. 56:2360–2369 (1990)). All data are means of samples from triplicate bottles for each treatment. The standard deviations for the congeners were within the limits of experimental error found in previous studies (Quensen, J. F., III, Appl. Environ. Microbiol. 56:2360–2369 (1990)).

Analysis. At the end of the incubation period, the cultures and controls were acidified and blended in a stainless steel blender (Sorvall Omni-mixer) and the residual PCBs were extracted with a mixture of hexane and acetone, using a modification of the procedure previously described for river sediments (Quensen, J. F., III, et al., Appl. Environ. Microbiol. 56:2360–2369 (1990)) with the following modifications. The ratio of hexane to acetone in the extraction solvent was changed to 7:3, and two centrifugation steps (3,000 rpm at room temperature) were included to separate the solvent and the aqueous phase containing the fungal mycelium. The florisil column which was used to clean up the hexane extract containing PCBs in the above-described procedure was not required in the extraction. Eighty to ninety-five percent (80 to 95%) extraction efficiency was obtained, which was consistent with previously published reports on PCB extraction from river sediments (Quensen J. F., III et al., Appl. Environ. Microbiol. 56:2360–2369 (1990)). High resolution PCB analysis was done by using capillary GC (Hewlett Packard model 5890 chromatograph with a 50-m Hewlett Packard Ultra-2 capillary column electron capture detector, and data system, as previously described (Quensen, J. F., III et al., Appl. Environ. Microbiol. 56:2360–2369 (1990)). Percent degradation was calculated by determining the net percent difference between the residual PCB concentration in experimental cultures and that in parallel heat-killed controls.

RESULTS

Degradation of Aroclors 1242 and 1254. Degradation of Aroclor 1242 and that of Aroclor 1254 by *P. chrysosporium*, as determined by high resolution GC analysis, were compared in LN, HN and ME media as shown in Table 2.

TABLE 2

Degradation of individual congeners in Aroclor 1260 by *P. chrysosporium*[a]

| Peak no. | Congener structure | Amt added (µmol/liter) | Degradation (%) of congeners | | |
|---|---|---|---|---|---|
| | | | LN | HN | ME |
| 38 | 236-25, 245-26, 24-34 | 0.4 | 18 (13) | 35 (9) | 38 (7) |
| 41 | 23-34, 234-4 | 0.1 | 19 (6) | 32 (5) | 33 (15) |
| 42 | 245-25, 235-24 | 0.8 | 26 (8) | 21 (6) | 34 (6) |
| 46 | 234-25, 2346-4, 235-35 | 0.1 | 42 (4) | 46 (4) | 67 (10) |
| 48 | 236-236 | 0.3 | 21 (8) | 11 (6) | 16 (8) |
| 49 | 34-34, 236-34 | 0.3 | 31 (6) | 24 (5) | 57 (5) |
| 50 | 2356-25 | 0.9 | 12 (6) | 8 (6) | 11 (6) |
| 51 | 235-236, 345-25, 2346-25 | 0.7 | 19 (5) | 8 (5) | 18 (5) |
| 52 | 245-34, 236-245, 2345-3 | 1.4 | 23 (4) | 17 (6) | 33 (3) |
| 54 | 235-245, 2346-35 | 0.3 | 6 (2) | 7 (6) | 10 (5) |
| 55 | 245-245 | 2.0 | 7 (4) | 4 (6) | 9 (2) |
| 56 | 234-236, 234-34 | 0.2 | 31 (3) | 17 (5) | 34 (9) |
| 57 | 2345-25 | 0.4 | 16 (3) | 10 (6) | 29 (1) |
| 58 | 2356-236 | 0.5 | 6 (3) | 2 (6) | 9 (2) |
| 61 | 234-245, 2356-34 | 3.0 | 18 (2) | 11 (6) | 29 (1) |
| 62 | 2346-34 | 0.3 | 7 (1) | 7 (7) | 18 (2) |
| 63 | 2356-235 | 0.2 | 3 (1) | 2 (7) | 2 (3) |
| 65 | 2356-245, 2345-246 | 0.6 | 4 (2) | 4 (7) | 8 (2) |
| 66 | 2346-245 | 0.4 | 4 (1) | 4 (7) | 8 (3) |
| 68 | 23456-25 | 0.2 | 1 (1) | 2 (10) | 4 (4) |
| 69 | 2345-236, 23456-24 | 0.8 | 9 (1) | 6 (7) | 17 (2) |
| 70 | 2356-234 | 0.4 | 4 (1) | 3 (7) | 9 (3) |
| 71 | 2346-234, 2345-34, 2356-2356 | 0.4 | 10 (2) | 8 (8) | 15 (3) |
| 73 | 2345-235, 23456-35 | 0.2 | 2 (1) | 4 (9) | 5 (4) |
| 74 | 2345-245 | 1.7 | 3 (1) | 4 (7) | 9 (3) |
| 78 | 2345-234 | 0.6 | 2 (0) | 3 (8) | 7 (3) |
| 79 | 23456-34 | 0.2 | 0 (0) | 0 (0) | 5 (8) |
| 80 | 2356-2345 | 0.5 | 2 (1) | 4 (8) | 7 (3) |
| 81 | 2345-2346, 23456-245 | 0.4 | 0 (0) | 2 (9) | 5 (4) |
| 83 | 23456-234 | 0.2 | 1 (4) | 1 (10) | 7 (4) |
| 85 | 2345-2345 | 0.4 | 0 (0) | 2 (10) | 5 (4) |
| 87 | 23456-2345 | 0.2 | 0 (0) | 1 (12) | 9 (4) |

[a]Experimental conditions and other details were as described in the footnotes for Table 1.

Values for net reduction (percent decrease by weight) in total PCB content for Aroclor 1242 was comparable (56.3 to 60.9%) for all the media. However, maximal degradation (30.5%) of Aroclor 1254 was observed with ME medium, while relatively low levels of degradation (21.6 and 10%, respectively) were seen with LN and HN media (FIG. 1).

Figure 2A:
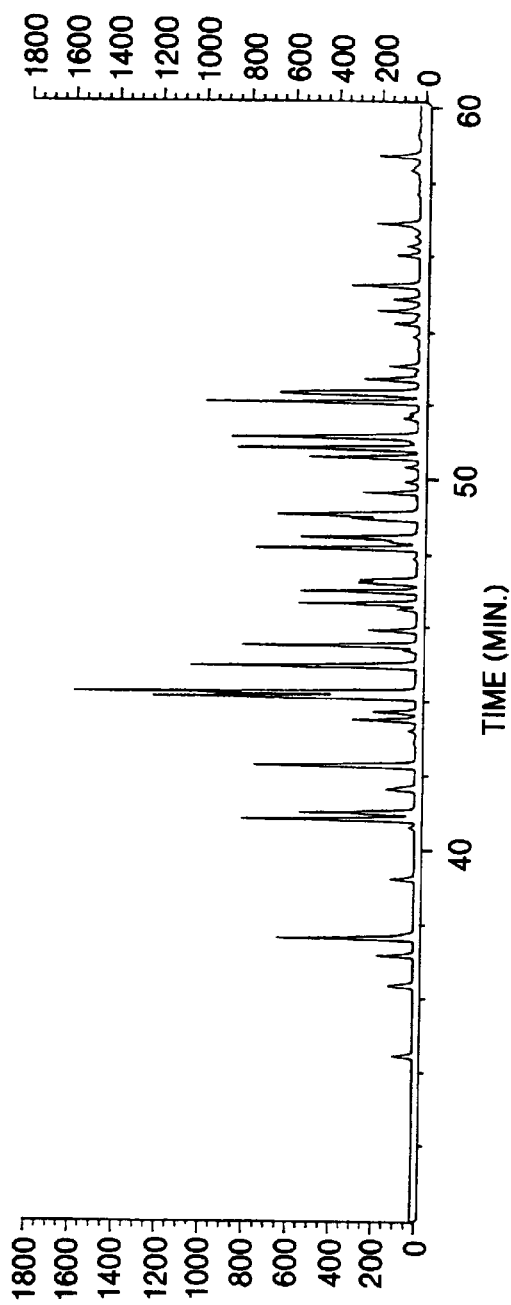
FIGS. 2A and 2B are graphs showing biodegradation of AROCLOR 1242 in maltose extract (ME) medium by *P. chrysosporium* as shown by the congener-specific GC analysis of residual PCBs in heat-killed control (FIG. 2) and in experimental culture (FIG. 2A) after 30 days of incubation. y-axis values represent detector responses, while x-axis values correspond to the retention times for different congener peaks in the GC run. The order and the congener structures of the GC peaks are the same as those presented in Table 1.
Figure 2B:
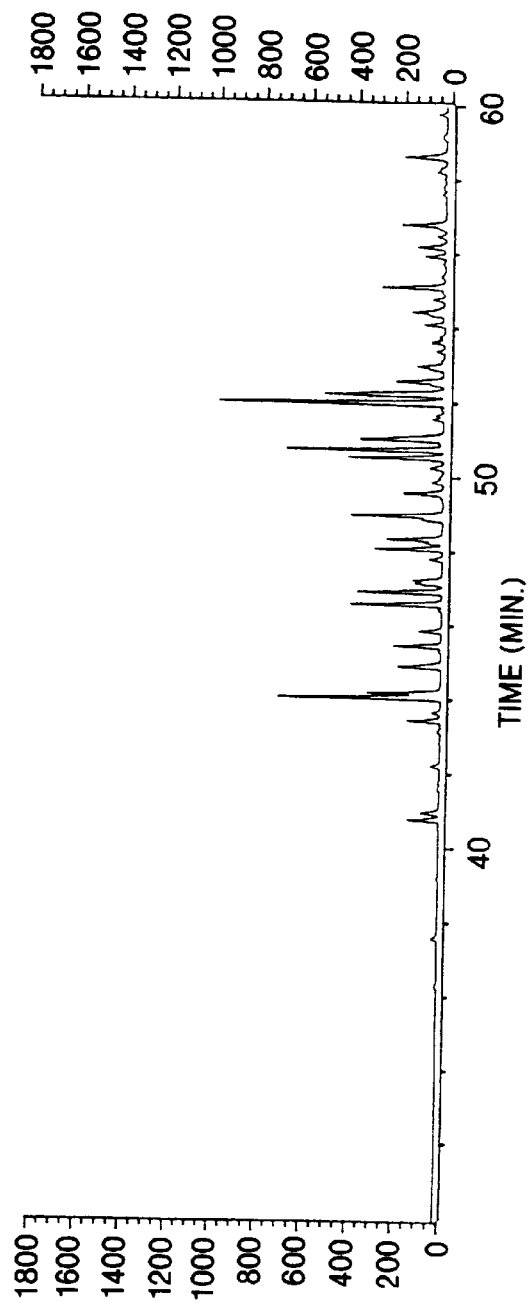

The extent of degradation of individual PCB congeners in Aroclor 1242 in LN medium and that in HN medium are presented in Table 1. The number and positions of chlorines on each congener are also given in Table 1. It should be noted that a few of the peaks represent more than one congener, as the GC technique used does not distinguish these. The results (Table 1 and FIGS. 2A and 2B) show that almost all the congeners in Aroclor 1242 were degraded, although the amount of degradation for each congener varied in the three media (LN, HN, and ME). Relatively high levels of degradation were seen for congeners eluting in peaks 1 to 23, while the congeners represented by peaks 24 and higher were degraded to a lesser extent, suggesting that the relative degradability of a congener decreases with the increase in the number of chlorine substitutions on the biphenyl nucleus (Table 1 and FIGS. 2A and 2B). The data further show that *P. crysosporium* is capable of transforming a variety of congeners with various degrees and positions of chlorine substitutions. For instance, congeners with ortho, meta and/or para substitutions were all degraded. Interestingly, ortho-substituted congeners with as many as three ortho chlorines were degraded, though the extent of their degradation was different under different culture conditions. For example, 2,2',3,6'-CB (GC peak 23) underwent 70.2% degradation in LN medium, compared with 61.0% degradation in HN medium and 81.5% degradation in ME medium (Table 1 and FIGS. 2A and 2B). Many of the congeners in Aroclor 1254 decreased substantially under both nitrogen-limited and nitrogen-sufficient culture conditions (Table 1). However, 50% of the congeners showed maximal degradation in ME medium compared with that observed in HN and LN media. Also, the highest loss in total PCB content was observed in the ME medium.

The results in FIG. 3 show time-dependent degradation of different PCB congeners in Aroclors 1242 and 1254 when incubated for 15 and 30 days in LN medium. Most of the congeners in both the Aroclors showed a higher level of degradation at the end of 30 days of incubation than at the end of 15 days. Degradation of some of the more-chlorinated congeners in Aroclor 1254 (e.g. peaks 51 through 78) was observed only in cultures incubated for 30 days. Similar effects of incubation were observed in HN medium. However, in ME medium, there was relatively little difference in the extent of degradation of a majority of the congeners between the 15- and 30-day incubation periods (data not shown).

Degradation of Aroclor 1260. It was of particular interest that *P. chrysosporium* showed substantial degradation of Aroclor 1260, a highly chlorinated mixture of PCB congeners (FIG. 1; Table 2). Degradation was observed in both nutrient-limited (ligninolytic) and nutrient-rich (non-ligninolytic) conditions. Among the three media used, the highest level of degradation was achieved in ME medium (17.6% by weight) and somewhat lower levels of degradation were observed in LN (10.76) and HN (8.46) media (FIG. 1). Most of the components of Aroclor 1260 were degraded (Table 2), though to various extents (1.6 to 66.5%), depending on the number and positions of chlorine substitutions on the biphenyl ring. The degradability of a given congener varied with the medium used (Table 2). Length of incubation (15 versus 30 days) had a similar effect on degradation of Aroclor 1260, in that many of the more-chlorinated congeners were degraded in 30 days but not in 15 days of incubation (data not shown)

Published reports (Bumpus, J. A., et al., Science 228:1434–1436 (1985); Eaton, D. C., Enzyme Microb. Technol. 7:194–196 (1985); and Thomas, D. R., et al., Biotechnol. Bioeng. 40:1395–1402 (1992)) on the degradation of PCBs by *P. chrysosporium* indicated mineralization of very low concentrations of radiolabeled PCBs to $^{14}CO_2$, in ligninolytic cultures in which LIPs and MNPs are known to be produced. For example, Eaton (Eaton, D. C., Enzyme Microb. Technol. 7:194–196 (1985)) reported about 9% mineralization of $^{14}$C-labeled Aroclor 1254 to $^{14}CO_2$ when a low concentration (0.25 ppm) was added to low-N (2.2 mM N) cultures of P. chrysosporium. In comparison, a 20 to 30% loss of 10 ppm of Aroclor 1254 occurred was observed in the present invention, as determined by GC analysis (FIG. 1). Substantial degradation of individual congeners in Aroclors 1242 and 1254 not only under nutrient-limited conditions but also under nutrient-rich conditions. These observations are significant from the standpoint of a potential application of P. chrysosporium for the degradation of PCBs in the environment, where nutrient concentrations vary from site to site. As nutrient limitation at certain contamination sites would lead to poor growth of the fungus, supplementation with nutrients might be needed for obtaining a higher mycelial mass of P. chrysosporium. In this context, results indicate that nutrient-rich conditions do not adversely affect degradation of PCBs by this organism. The data show that some of the common congeners in Aroclors 1242 and 1254 are not degraded (on a percent basis) to the same extent in the two mixtures (Table 1). For instance, percent degradation of peak 38 is lower in Aroclor 1254 than in Aroclor 1242 (Table 1). One reason for these observed differences is that the two Aroclor mixtures vary quantitatively in their congener composition. In the specific example given above peak 38 has three congeners, namely 236-25, 24-34, and 245-26, whose concentrations (weight percent of the total PCBs) are 2.87, 1.66, and <0.05 in Aroclor 1242 but 6.02, 0.59, and <0.05 in Aroclor 1254 (Schulz, D. E., et al., Environ. Sci. Technol. 23:852–858 (1989)). The observed difference in percent reduction in peak 38 in the two Aroclors can, therefore, be explained if the 24-34 congener in each Aroclor is degraded but not the 236-25. This explanation also holds true for many of the peaks common to the two Aroclors. Furthermore, the two Aroclors also differ qualitatively in their congener composition; this may affect the relative reactivity of a given congener in the two mixtures. Also, as the degradation proceeds in a PCB mixture, the metabolites released from some of the congeners can further affect the relative reactivity of a given congener and this metabolite effect on relative reactivity may vary in the two Aroclor mixtures and in different media.

In previous studies using aerobic bacterial isolates, significant degradation of most of the congeners in Aroclor 1242 and some of the congeners in Aroclor 1254 have been reported (Bedard, D. L., et al., Appl. Environ. Microbiol. 53:1094–1102 (1987); Boyle, A. W., et al., Biodegradation 3:285–298 (1992) ; and Kohler, H. P. E., et al., Appl. Environ. Microbiol. 54: 1940–1945 (1988)). However, unlike P. chrysosporium, these isolates required the addition of biphenyl for inducing the degradation activity and showed a preference for congeners with unsubstituted 2,3 positions on the PCB moiety (Bedard, D. L., et al., Appl. Environ. Microbial. 53:1094–1102 (1987); and Boyle, A. W., et al., Biodegradation 3:285–298 (1992)). Substantial degradation of PCB mixture Clophen A 30 (which is considered equivalent to Aroclor 1242 in chlorine content) by Aspergillus niger (Dmochewitz, S., et al., Chemosphere 17:11–121 (1988)) was observed, but congeners with substitutions in the 4- or 2,5(3,6)-positions positions tended to persist. Moreover, A. niger was found to be incapable of transforming the more-chlorinated PCB mixtures Clophen A 50 and Clophen A 60 (which are equivalent to Aroclors 1254 and 1260, respectively). In contrast, the present invention shows that P. chrysosporium is capable of substantial degradation of various congeners in all of the three Aroclors tested. Moreover, P. chrysosporium does not show any noticeable specificity for congeners with ortho, meta, or para chlorine substitutions in Aroclors. The relative nonspecificity towards degradation of differentially substituted congeners observed in the present invention is very advantageous for bioconversion of PCB-contaminated sites which usually contain many different PCB congeners. The nonspecificity of degradation might be due to a free radical mechanism of attack. Such a free radical mechanism of attack has previously been reported to have a role in the degradation of a wide range of other aromatic pollutants such as dioxins and chlorophenols by the fungus (Hammel, K. E., Oxidation of aromatic pollutants by lignin-degrading fungi and their extracellular peroxidases, p. 41–60. In H. Sigel and A. Sigel (ed), Metal ions in biological systems, vol. 28, Degradation of environmental pollutants by microorganisms and their metalloenzymes. Marcel Dekker, Inc, New York (1992)). However, our data show a higher rate of degradation of less-chlorinated congeners (peaks 1 through 23) than of the more-chlorinated congeners (peaks 24 and higher) in Aroclor 1242 by this organism (Table 1). This suggests that chlorine substitution does, to some extent affect oxidative attack by the fungal enzyme system but to a lesser extent than for the bacterial dioxygenases (Abramowicz, D. A., Crit. Rev. Biotechnol. 10:241–251 (1990)).

Degradation of Aroclor 1260 by P. chrysosporium is particularly significant. This is the first conclusive demonstration of the degradation of PCBs in Aroclor 1260 by any microorganism. Although reductive dechlorination of certain components of Aroclor 1260 has been reported in earlier work (GE Progress Report. General Electric Company Research and Development program for the destruction of PCBs: twelfth progress report for the period Aug. 1, 1992–Jul. 31, 1993. General Electric Co. Corporate Research and Development, Schenectady, N.Y. pages 117–127 and 129–141 (1993); Quensen, J. F., III, et al., Appl. Environ. Microbiol. 56:2360–2369 (1990)), there was no net decrease in the molar quantity of PCBs in those anaerobic transformations. An 18.4% decrease in the molar quantity of PCBs in Aroclor 1260 with P. chrysosporium was obtained with the present invention.

It is found that P. chrysosporium substantially degrades both less-chlorinated and more-chlorinated PCB mixtures (Aroclors 1242, 1254 and 1260). Net degradation of most of the individual PCB congeners in these formulations was observed. The fungus does not appear to show specificity for ortho-, meta-, or para-substituted PCB congeners.

P. chrysosporium ME446 (ATCC 34541) is available from the American Type Culture Collection, Rockville, Md. and is generally available from numerous sources. Other similar strains are well known to those skilled in the art.

EXAMPLE 2

Control

Compost windrows are constructed at the site with dimensions similar to those normally used at large scale windrow composting facilities with each windrow containing approximately 50–80 yd of material consisting of contaminated soil and yard trimmings amendment. Typically, considerable spatial variability is expected in the concentration of PCBs at contaminated sites. Hence, the contaminated soil is excavated and homogenized to provide a uniform PCB concentration. Subsequently, the contaminated soil is amended with yard trimmings at levels of 5%, 20%, 50% or 80% and physically mixed to uniformly distribute the PCBs throughout the compost mixture. The windrows are formed from these mixtures, and then turned periodically using a front-end loader or other appropriate equipment. If smaller amounts of PCB contaminated soil or other material is to be treated (ca. 1 yd³), the composting process should be carried out within a contained vessel, such as COMPOSTUMBLER (Lititz, Pa.), which are turned weekly. Other containerized compost systems such as the AG-RENU system (Middletown, Ohio), or the system developed by Green Mountain Technologies (Whitingham, Vt.), can be used.

The composting process is monitored by making measurements of oxygen concentration and temperature each week and samples are taken each month to determine total organic matter, moisture content, pH, bulk density, C:N ratio as well as the concentration of PCBs. A composite sampling approach is utilized to reduce sampling variability while at the same time minimizing the number of samples that must be analyzed. For example, five random samples from a compost windrow is thoroughly mixed together, and a subsample taken for extraction and analysis. The mean concentration of a component in the compost windrow is estimated by taking the mean of five such composite samples. The standard error associated with this mean is the standard deviation of the five samples analyzed, with four degrees of freedom. Sample variance influences the actual number of such composite samples that must be analyzed to demonstrate a significant reduction in total PCB concentration or a reduction in PCB concentration below a set target level.

Experimental Degradation

The rate and extent of PCB degradation in contaminated soils is enhanced through bioaugmentation with certain lignin-degrading fungi such as *P. chrysosporium* grown on malt extract medium of Example 1 and then inoculated. The fungal inocula used for bioaugmentation is prepared by inoculating yard trimmings, wood chips or grains in four liter polyethylene bags with a spore suspension of the fungus prepared as previously described (Lamar, R. T. and D. M. Dietrich, Appl. Environ. Microbiol. 56:3093–3100 (1990)). These are then incubated at appropriate temperature to allow growth of the fungus. Subsequently, the inoculum is blended with mixtures of yard trimmings and contaminated soil as described previously. The moisture level is adjusted to 90 to 100% of the water holding capacity of the matrix and the material is formed into windrows or placed in a composting vessel such as Lescha K-36 (Mulhausen, Germany) in-vessel composting system.

The compost windrows or in-vessel composting processes are managed and monitored as described. The growth of *P. chrysosporium* is inhibited above 40° C. Hence any of several strategies are employed to maintain temperatures at or below 40° C. These include forced aeration, reduced amounts of yard trimmings (i.e. increased amounts of soil), smaller windrow dimensions or addition of the fungal inoculum after the high temperature phase has been completed. The composting process is closely monitored to determine the rate and extent of composting and of PCB degradation.

It is intended that the foregoing description be only illustrative of the present invention and that the present invention be limited only by the hereinafter appended claims.

We claim:

1. A method for degrading a mixture of polychlorinated biphenyls (PCBs), having an average of between 3 and 6 chlorine atoms per biphenyl and containing up to about 60% by weight of the chlorine atoms, in a soil which comprises the following steps:

(a) growing *Phanerochaete chrysosporium* in a medium consisting essentially of a first carbon source and a first nitrogen source under nutrient-rich, non-ligninolytic conditions wherein the first carbon source is present in an amount equivalent to at least 56 mM glucose as the carbon source and the first nitrogen source is present in an amount equivalent to at least 24 mM of ammonium ion as the nitrogen source, which growing is without producing lignin peroxidase and Mn(II)-dependent peroxidases, before addition to the soil to produce *Phanerochaete chrysosporium* cells which can degrade the PCBs;

(b) mixing the soil with the *Phanerochaete chrysosporium* of step (a), a second carbon source and a second nitrogen source in addition to and different from the first carbon source and first nitrogen source under the same nutrient-rich non-ligninolytic conditions as in step (a) in the soil; and (c) degrading of the mixture of polychlorinated biphenyls in the soil with the *Phanerochaete chrysosporium* to degrade the PCBs in the soil under the nutrient-rich non-ligninolytic conditions in the soil.

2. The method of claim 1 wherein the *Phanerochaete chrysosporium* is ATCC 34541.

3. The method of claim 1 or 2 wherein malt extract is the second carbon source and wherein there is between 0.1 and 5 percent of the malt extract.

4. The method of claim 1 wherein the second nitrogen source is an animal protein.

5. The method of claim 1 wherein the second nitrogen source is a vegetable protein.

6. The method of claim 1 wherein the second nitrogen source is an inorganic nitrogen containing salt.

7. The method of claim 1, 4 or 5 wherein the soil in step (b) contains up to 5 percent by weight malt extract as the second carbon source and more than 56 mM glucose as a third carbon source.

8. The method of claim 1 wherein the first carbon source is a simple sugar and the first nitrogen source is an ammonium ion.

9. The method of claim 8 wherein the first carbon source in addition comprises malt extract.

10. The method of claim 1 wherein the first carbon source is a simple sugar.

11. The method of claim 1 wherein the non-ligninolytic conditions in step (a) are provided by 56 mM glucose as the first carbon source and 24 mM ammonium ion as the first nitrogen source.

* * * * *

UNITED STATES PATENT AND TRADEMARK OFFICE
CERTIFICATE OF CORRECTION

PATENT NO. : 6,107,079
DATED : August 22, 2000
INVENTOR(S) : Jagjit S. Yadav, Chilekampalli A. Reddy, John F. Quensen and James M. Tiedje It is certified that error appears in the above-identified patent and that said Letters Patent is hereby corrected as shown below:

Column 4, Table 1, line 11, "98(9)" should be -98(0)-.

Figure 3A:
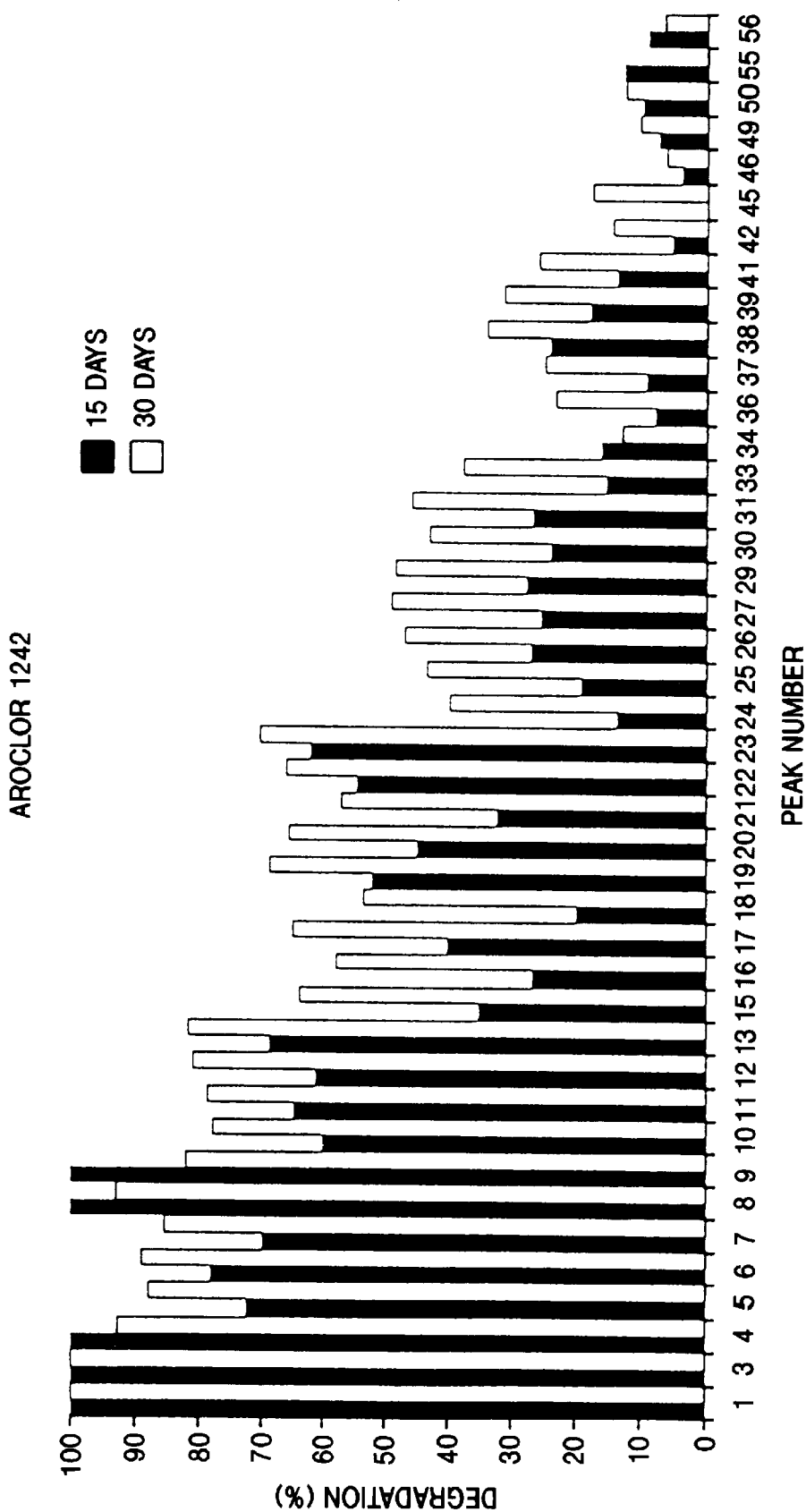
FIG. 3A is a graph showing effect of length of incubation period on the percent degradation of different PCB congeners in AROCLORS 1242 and 1254 by *P. chrysosporium* in LN medium. Peak numbers (x-axis, FIG. 3B) represent different congeners in each AROCLOR, as defined in Table 1. Values presented are means of triplicate samples.
Figure 3B:
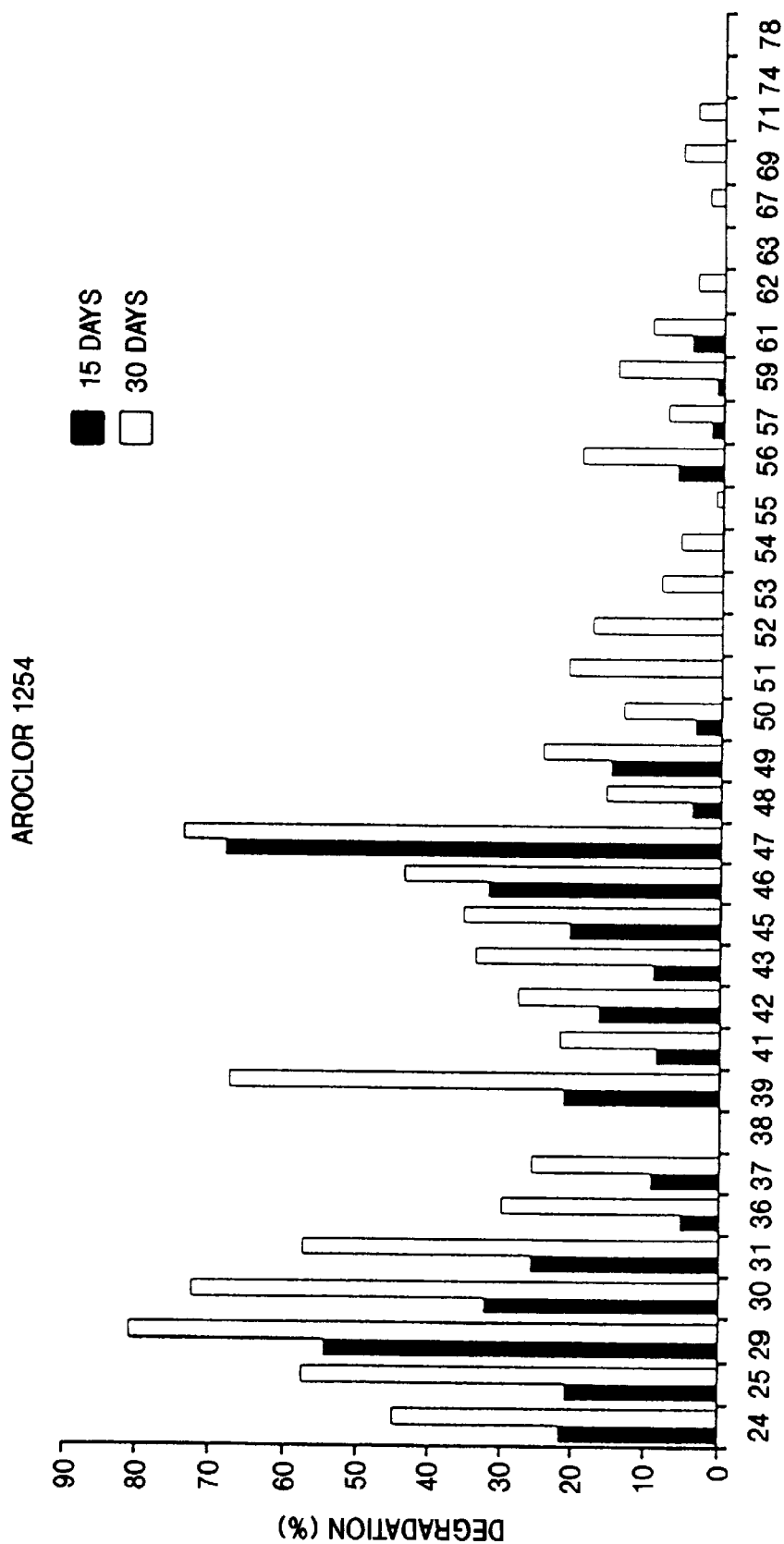

Column 10, line 32, "Fig. 3" should be -Figs. 3A and 3B-.

Column 10, line 53, "(8.46)" should be -(8.4%)-.

Column 11, line 63, "positions" (second occurrence) should be deleted.

Column 12, line 59, "50-80 yd" should be -50-80 yd$^3$-.

Signed and Sealed this

Twenty-ninth Day of May, 2001

Attest:

NICHOLAS P. GODICI

Attesting Officer    Acting Director of the United States Patent and Trademark Office